(12) United States Patent
Gheshlaghi et al.

(10) Patent No.: US 8,329,446 B2
(45) Date of Patent: Dec. 11, 2012

(54) GREEN MOLD INHIBITOR

(75) Inventors: Nader Gheshlaghi, Richmond Hill (CA); Jack Verdellen, Campbellville (CA)

(73) Assignee: Monaghan Mushrooms Ltd., Campbellville, Ontario (CA)

( * ) Notice: Subject to any disclaimer, the term of this patent is extended or adjusted under 35 U.S.C. 154(b) by 1173 days.

(21) Appl. No.: 12/037,308

(22) Filed: Feb. 26, 2008

(65) Prior Publication Data

US 2009/0214502 A1     Aug. 27, 2009

(51) Int. Cl.
*A01N 25/00* (2006.01)
*A01N 25/32* (2006.01)
*A01N 63/00* (2006.01)
*C12N 1/20* (2006.01)

(52) U.S. Cl. ............... 435/252.5; 424/93.462; 424/405; 424/406; 435/839

(58) Field of Classification Search .................. None
See application file for complete search history.

(56) References Cited

U.S. PATENT DOCUMENTS

| | | | |
|---|---|---|---|
| 5,762,928 A | 6/1998 | Bolkan et al. | |
| 5,919,447 A * | 7/1999 | Marrone et al. | 424/93.461 |
| 6,004,774 A * | 12/1999 | Marrone et al. | 435/41 |
| 6,029,394 A | 2/2000 | Kananen et al. | |
| 6,041,544 A | 3/2000 | Kananen et al. | |
| 6,061,951 A | 5/2000 | Pia | |
| 6,077,506 A * | 6/2000 | Marrone et al. | 424/93.461 |
| 6,245,551 B1 | 6/2001 | Lehman et al. | |
| 6,586,231 B2 | 7/2003 | Lehman et al. | |
| 6,635,245 B1 | 10/2003 | Lehman et al. | |
| 6,960,342 B2 | 11/2005 | Wu et al. | |

FOREIGN PATENT DOCUMENTS

CA     2271118     5/1998

OTHER PUBLICATIONS

AgraQuest, Inc. and Sylvan Inc. Form Strategic Alliance to Introduce Innovative Green Mold Protection in Mushrooms,http://www.agraquest.com/news-media/pressreleases/20081006.html, 2008.
Beyer et al., "Green Mold of Mushrooms," Dec. 19, 2007, http://mushgrowinfo.cas.psu.edu/Trichoderma%20Green%20Mold.html.
Chittihunsa et al., "Screening of *Bacillus* spp. Suppresing the Infection of *Trichoderma* sp. In Mshroom Cultivation," KMITL Sci. Tech. J., vol. 7, No. S1, pp. 19-27 (2007).
Gheshlaghi et al., "Exploration of Symbiotic Relationships between Green Mold & a Biological Control Agent," Research and Development Rol-land Farms Ltd., Campbellville, Ontario, Canada. (2007).
Moita et al., "Optimisation of Physical Factors on the Production of Active Metabolites of *Bacillus subtilis* 355 Against Wood Surface Contaminant Fungi." Int. Biodeterior. Biodegrad, vol. 55, pp. 261-269(2005).
Pennsylvania State University, College of Agriculture, Extension Service, "Six Steps to Mushroom Farming", http://www.mushroominfo.com/grow/sixteps.html, Dec. 23, 2007.
Serenade® Fungicide Receives EPA Registration for Cereal, Pulse, Canola and Berry Crops in the U.S., May 16, 2008 http://www.agraquest.com/news-media/pressreleases/20080516.html.
Velazquez-Cedeno et al., "Role of *Bacillus* spp. In Antagonism Between *Pleurotus Ostreatus* and *Trichoderma Harzianum* in Heat Treated Wheat-Straw Substrates." Bioresour. Technol., vol. 99, pp. 6966-6973 (2008).

* cited by examiner

*Primary Examiner* — Debbie K Ware
(74) *Attorney, Agent, or Firm* — Occhiuti Rohlicek & Tsao LLP

(57) ABSTRACT

The present invention provides a biocontrol agent for the prevention and/or reduction of mold during mushroom production. In particular, the invention utilizes *Bacillus* spp. as an agent for the control of mold caused by *Trichoderma* spp. The *Bacillus* spp. is a biologically pure culture of *Bacillus subtilis* strain J-P13.

7 Claims, 20 Drawing Sheets

A

B

C

A

B

A

B

A

B

C

A

B

A

B

US 8,329,446 B2

GREEN MOLD INHIBITOR

FIELD OF INVENTION

The present invention relates to mushroom cultivation and products that prevent the development of mold on mushrooms.

BACKGROUND OF THE INVENTION

The market for mushrooms continues to grow each year. This is due to an increasing interest in the culinary, nutritional and health benefits of mushrooms. The commercial production of mushrooms, however, is a complex procedure. It involves a series of steps including compost preparation, compost pasteurization, inoculating the compost with spawn, incubation to allow colonization of the compost with mushroom mycelia, pinning and cropping. Contamination with a pathogenic agent at any of these stages can result in serious yield losses.

The term "mushroom" is used herein to refer to various types of mushrooms. This includes the most familiar cultivated mushroom, *Agaricus bisporus* and also includes other types of mushrooms such as oyster mushrooms, crimini mushrooms, portobello mushrooms and shitake mushrooms, just to mention a few.

A major threat to successful large scale mushroom production is green mold. Green mold is caused by infestation with *Trichoderma*. Various types of *Trichoderma* spp. can result in a green mold infestation. A particularly pathogenic strain, identified as *Trichoderma harzianum* biotype 4, was responsible for a large green mold epidemic in the United States during the 1990's. When spawned mushroom beds are infested with *Trichoderma* spp. mold, non productive areas occur on the casing surface resulting in serious yield losses. Compost infestation can result in green sporylation which can turn into black patches uncolonized by mushroom mycelia.

Various attempts have been made to control infestation with green mold. For example, U.S. Pat. No. 6,061,951 describes a mushroom bed cover. The invention described therein involves the use of a cover which includes a series of holes or vents that are selected to control the $CO_2$ rates and oxygen rates during spawning so as to lower the rate of green mold. While this cover may reduce the rates of green mold infestation, it does not completely prevent it. In addition there may be other disadvantages associated with covering the beds including excessively high $CO_2$ content and over heating of the compost.

Another attempt at controlling green mold is described in U.S. Pat. No. 5,762,928. This patent describes the use of a composition comprising *Pseudomonas aeruginosa* which can be applied to compost, spawn or supplement to prevent or inhibit the growth of green mold. While the *Pseudomonas* composition was shown to have some effect in inhibiting green mold, the use of *Pseudomonas* as a large scale deterrent for green mold is not feasible since *Pseudomonas* is associated with several pathogenic states in humans.

While biocontrol agents have been shown to have some success in preventing mold on certain types of plants, control of mold in mushroom production provides a unique challenge. Since mushrooms, like mold, are fungi, agents that kill contaminating mold may also adversely affect the mushrooms.

Thus, there remained an unmet need for an agent that can control green mold without adversely affecting production of the mushrooms. The agent should also be safe for human consumption.

SUMMARY OF THE INVENTION

The present invention provides agents, compositions and methods for the prevention and/or control of contamination with mold during the mushroom production process.

In a first aspect of the invention, a method of inhibiting green mold in mushrooms caused by *Trichoderma* spp. is provided. The method comprises administering an effective amount of a composition comprising *Bacillus* spp. The *Bacillus* may be applied directly into the mushroom compost or it may be incorporated into a mushroom spawn supplement. In a preferred embodiment the *Bacillus* is formulated into a spray that can be applied to the mushroom beds. The spray may be aqueous in composition.

In a preferred embodiment, the *Bacillus* spp. is *Bacillus subtilis*.

In a further preferred embodiment, the *Bacillus* spp. comprises strain J-P13.

In another preferred embodiment, the composition further comprises a carrier. Some examples of carriers include, but are not limited to microcarrier beads, granules, particles, peptone solution, oil, wax, gel and water. In a preferred embodiment, the carrier is water.

In another aspect of the invention, a biologically pure culture of *Bacillus* spp. strain J-P13 is provided.

In yet another aspect, a process for controlling *Trichoderma* spp. in a plant or a plant production component is provided. The process comprises applying a composition containing *Bacillus* spp., preferably *Bacillus* spp. more preferably *Bacillus* spp. strain J-P13. In a preferred embodiment the plant is a mushroom or mushroom propagating component.

BRIEF DESCRIPTION OF THE DRAWINGS

These and other features of the invention will become more apparent from the following description in which reference is made to the appended drawings wherein.

FIG. 12 shows a tray found with green mold on which a *Bacillus* spp. culture was sprayed, and the results observed after 48 hours;

FIG. 13 shows A) a tray with green mold, and B) after being sprayed with *Bacillus* spp. culture that inhibited the green mold from contaminating the remainder of the tray;

FIG. 14 shows sequential observations of A) mold growing on trays; B) a tray after it was sprayed, and C) a tray after approximately 2 days;

FIG. 15 shows observations of A) mold growing on a tray, and B) the tray approximately 2 days after it was sprayed;

FIG. 16A shows a sample that includes *Bacillus* culture and green mold additions, FIG. 16B shows the top, FIG. 16C shows the overturned, and FIG. 16D shows the broken up sample without any further green mold growth;

FIG. 17A shows the initial inoculation of bacteria, FIG. 17B shows day one of culture in a small container with precase, FIG. 17C shows green mold growing in the bottom half of container, FIG. 17D illustrates that mycelia were able to grow throughout the entire sample as the green mold was irradicated;

FIG. 18 shows a growth curve of *Bacillus subtilis* J-P13 in water;

FIG. 19 illustrates graphically bacterial concentration in a spawning water tank after the addition of 5 to 7 days of growth of 18.9-20 L distilled water bottles with *Bacillus subtilis* J-P13 culture; and FIG. 20 shows confirmation plates with 10 μL spawn tank water with 100% complete mold coverage. 50% inhibition was calculated to be $1.6\times10^6$ CFU per lawn of green mold growth. The above plates were made using the tank water after day 5 (A) and day 8 (B) onto PDA and incubated at 25.0° C. for 72 hours.

DETAILED DESCRIPTION

Infestation with *Trichoderma* spp. is a major concern for commercial mushroom producers. It can lead to devastating crop losses and even to complete loss of the crop resulting in shut-down of production. Various species of *Trichoderma*, including but not limited to *T. harzianum, T. aggressivum, T. viride, T. inhamatum, T. atroviride* may be responsible for mold contamination of mushrooms at any stage of their growth.

The present invention provides a novel agent for the control and/or prevention of green mold at all stages of mushroom production. The biocontrol agent of the present invention comprises *Bacillus* spp. The agent may comprise, for example, *Bacillus velezensis, Bacillus amyloliquefaciens, Bacillus lichenformis, Paenibacillus favisporus* or another *Bacillus* strain. A strain of *Bacillus subtilis* that is particularly effective in preventing and controlling green mold is provided.

The invention comprises a composition containing an amount of *Bacillus subtilis* effective to prevent or treat contamination with green mold (*Trichoderma harzianum*). Effective concentrations of bacteria are any which inhibit the development of green mold. Exemplary concentrations range from about $1.5\times10^6$ CFU/ml to about $5\times10^7$ CFU/ml, preferably about $5\times10^6$ CFU/ml.

The bacterial composition may be provided as a suspension or slurry from culture or the bacteria may be combined with a suitable carrier such as oils, peptone, water or any other suitable carrier that is safe for human consumption. For economy and ease, water is a preferred carrier. Other additives which enhance the effectiveness of the bacteria or which promote mushroom growth may be included in the bacterial composition. The bacteria may also be provided on the surface of a solid carrier or encapsulated. Alternatively, the bacteria may be freeze-dried and applied as a powder or dust.

The composition can be applied using conventional methods such as dipping, spraying or brushing. The composition can also be formulated into a coating which can be applied to surfaces such as casing or mushroom bed covers.

The *Bacillus* composition can be applied at any stage of the mushroom production process. It is preferably added to the mushroom compost. Alternatively, it can be added to the spawn before it is mixed with the compost or to the casing. The composition can also be applied to trays or to the mushroom crop. The composition can be used to prevent an infestation of green mold or to treat an infection that has occurred.

Referring now to the figures, the efficacy of *Bacillus subtilis* as an biocontrol agent for *trichoderma hazianum* is demonstrated. Compositions comprising *Bacillus subtilis* were shown to be both fungistatic and fungicidal.

A bacterial colony was isolated from an air fallout plate where it showed inhibition of surrounding green mold. The colony halted the growth of green mold that was also observed on the same plate. Once this inhibitor was purified and cultivated, its antimicrobial production potential was shown by the inhibition of known *Trichoderma* spp. spores. The antifungal activity was confirmed by present/absent tests to observe fungicidal or fungistatic actions, directly plated material samples with green mold contamination, as well as small tray experiments with a suitable carrier incorporated in the compost, supplement, spawn etc.

The air fall out plates (potato dextrose agar plates) were placed on a horizontal surface for a maximum of one hour. Observations of current environmental factors, such as number of employees, activities in proximity to plate location, external stimuli were recorded. Plates were sealed and incubated at 22-25° C. for 48-72 hours for optimal recovery of mold spores. As shown in FIG. 1, developmental *Trichoderma* filaments were present as white lobular hyphae. On one plate, a bacterial colony had a halo surrounding its perimeter where the *Trichoderma hyphae* seemed to be growing around, not over, the colony as shown in FIG. 3. The colony was isolated and replated. As shown in FIG. 2, isolated colonies were cream coloured with an irregular margin, creatorform elevation, opaque, matte, and approximately 2 mm in diameter.

After one week, the presence of *Trichoderma* was confirmed via microscopic observations. As shown in FIG. 4, conidiophores with short side branches, short inflated phialides (flask shaped), and smooth, small conidia that were generally green, ranging from globose to ellipsoidal were present. The inhibiting bacterial colony was gram positive with endospores, ellipsoidal, with single randomly located cells as well as the occasional chain as shown in FIG. 5. Biochemical tests indicated that the bacterial culture was catalase positive, and was able to grow in minimally defined media with no growth factors under aerobic conditions. This isolate was named J-P13.

Isolate J-P13 was identified based on a 16S rRNA gene sequence, and compared with Global GeneBank Database by the University of Guelph, Laboratory Services. The results indicated that P13 culture matched more than one *Bacillus* species. Further investigation resulted with a 0.936 similarity index with *Bacillus subtilis*. A similarity index was defined as a numerical value expressing how closely the fatty acid composition of an unknown isolate compared with that of the MIDI database match, where SI of 0.6 to 1.0 indicated an excellent match with 1.0 being the highest. Two deposits of microorganisms were made on Sep. 9, 2009 with the International Depositary Authority of Canada ("IDAC") under Accession Numbers 090909-01 and 090909-02.

Figure 1:
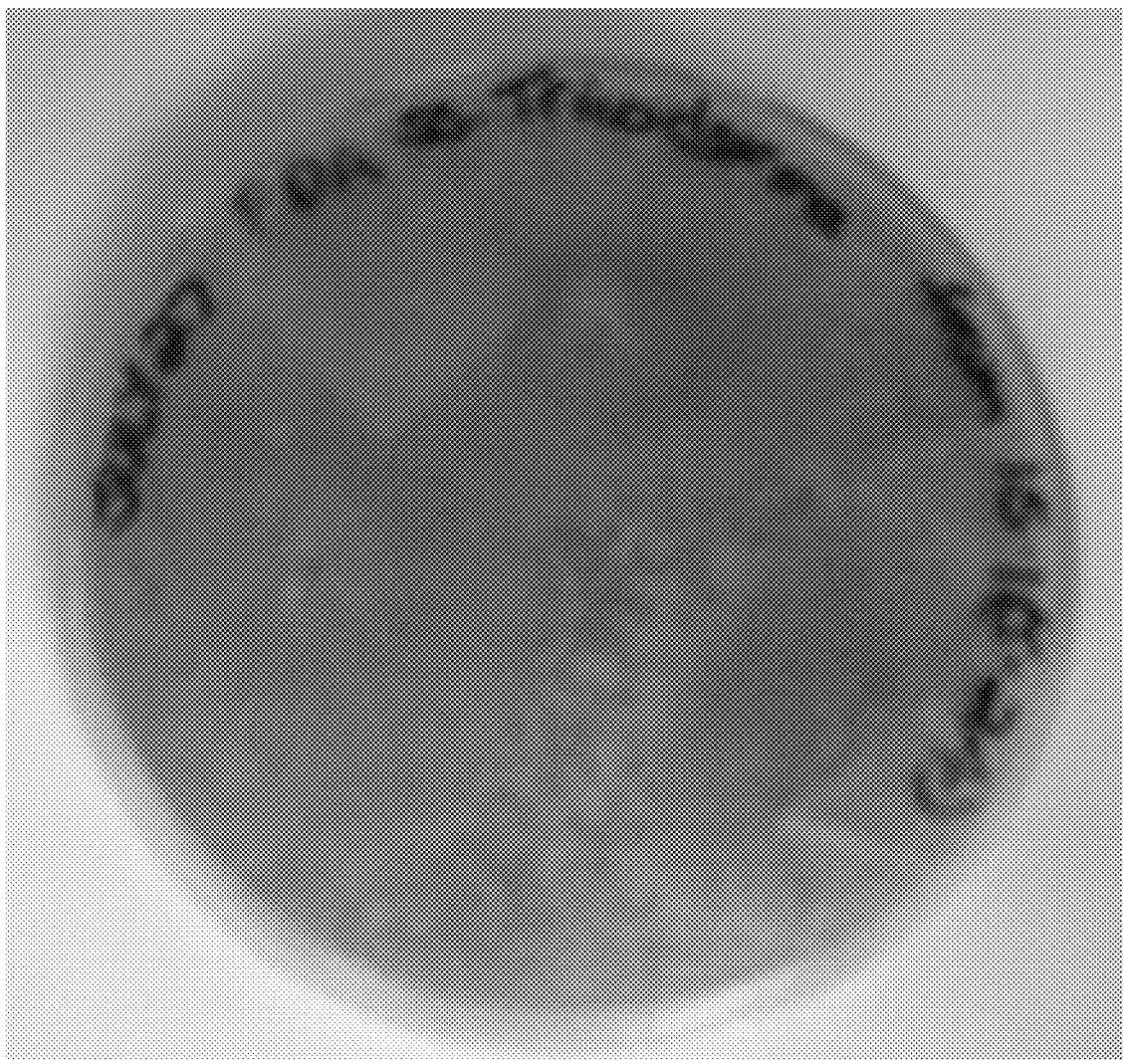
FIG. 1 shows a macroscopic view of *Trichoderma* spp. from SAC area, collected via air sample.
Figure 2:
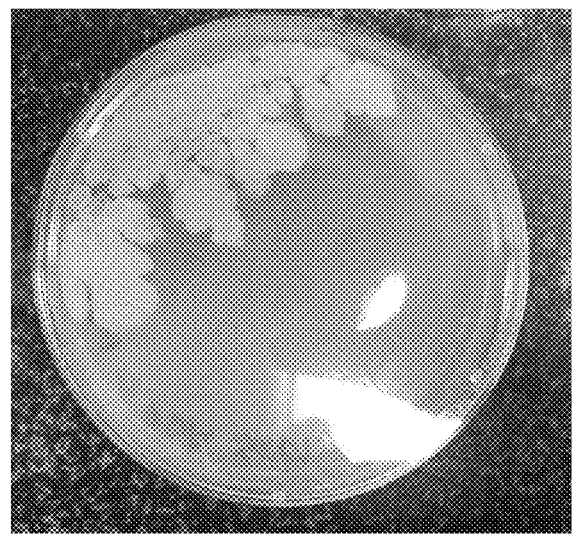
FIG. 2 shows a macroscopic view of *Bacillus* spp., isolated from outside of a pinning room collected via air sample and plated onto a) PDA, b) MEA, and SMA.
Figure 2:
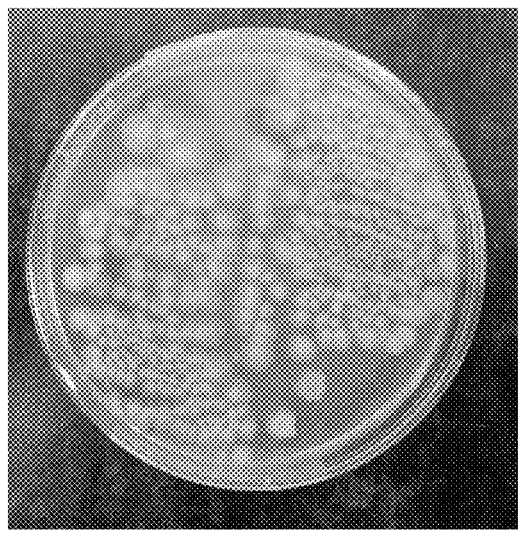
Figure 2:
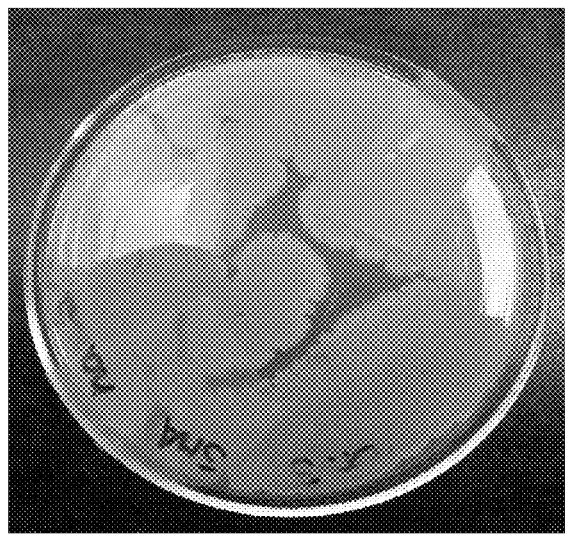
Figure 3:
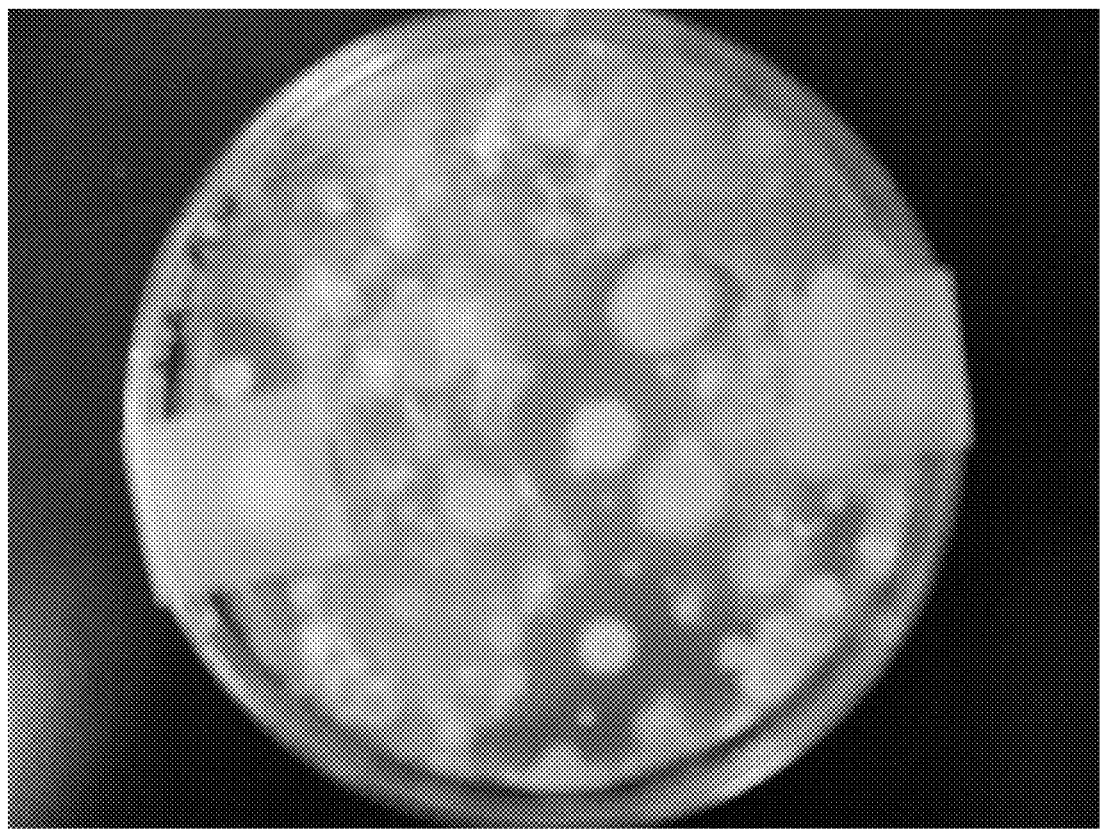
FIG. 3 shows an air sample plate with the original J-P13 colony (*Bacillus* spp.) showing inhibition of green mold growth.
Figure 4:
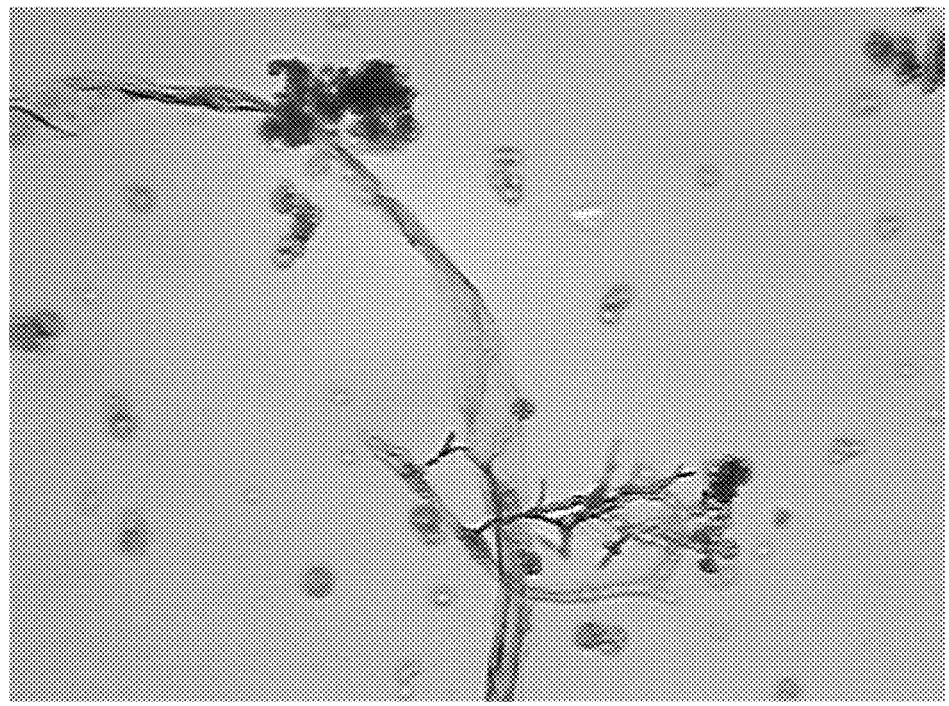
FIG. 4 shows microscopic views of *Trichoderma* spp. from a pinning room in which the slide was made from spores directly from the compost.
Figure 4:
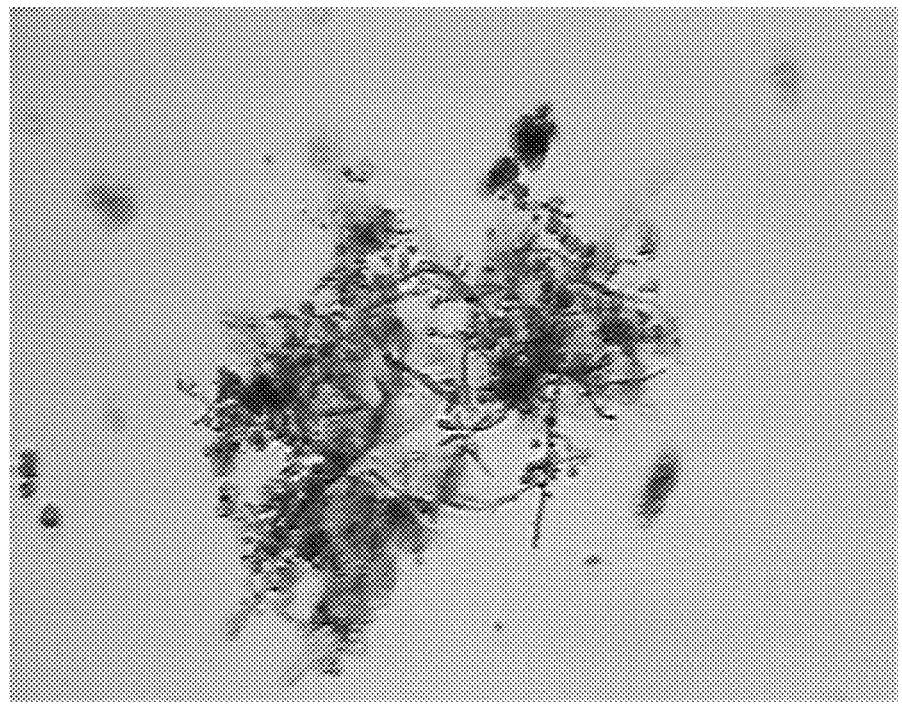
Figure 5:
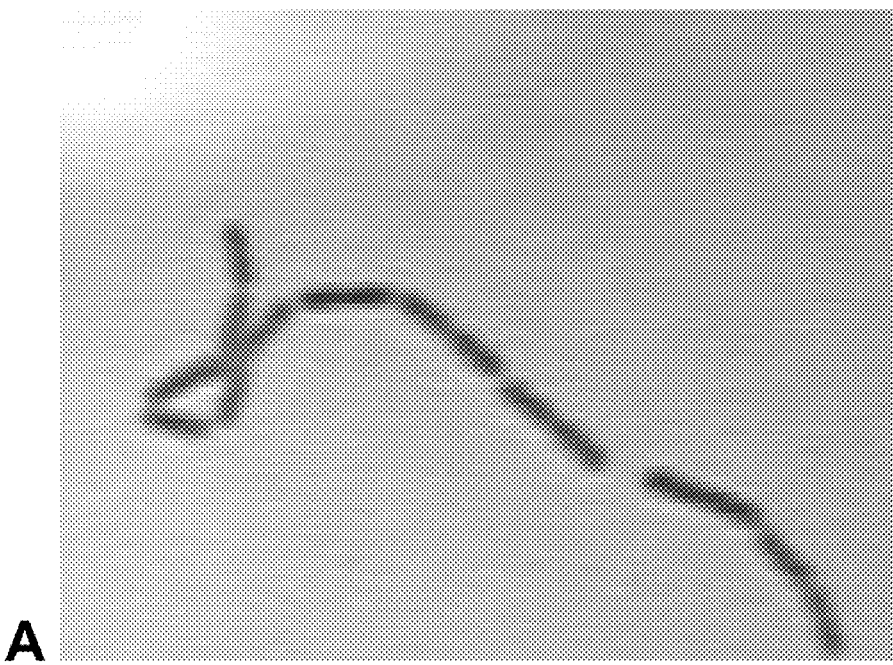
FIG. 5 shows a microscopic view of presumptive *Bacillus* spp. cultures from an NA isolate plate where both were gram stained. Image A) is a slide from an isolate culture harvested in 1% peptone; and Image B) is from an isolate during stationary phase.
Figure 5:
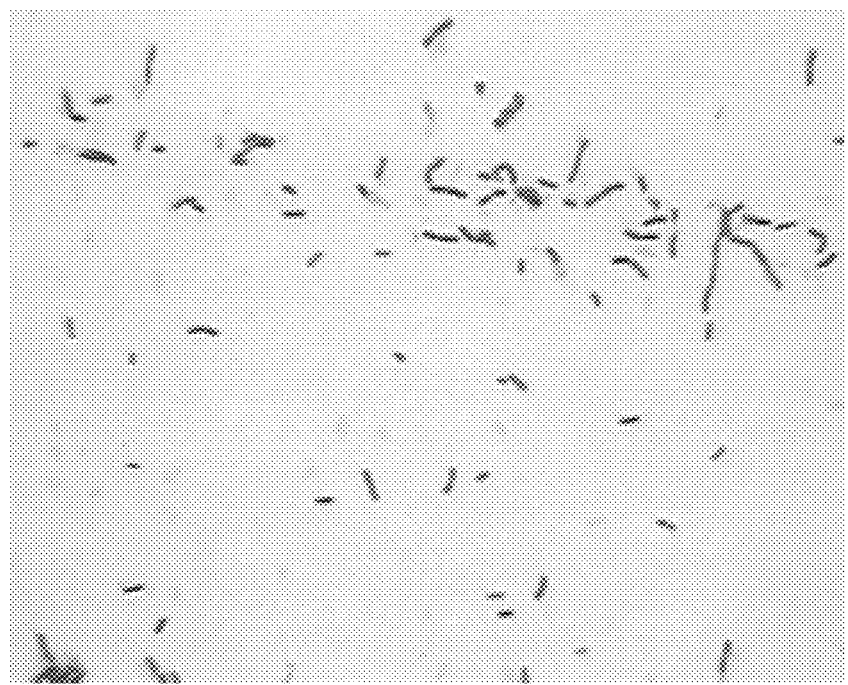
Figure 6:
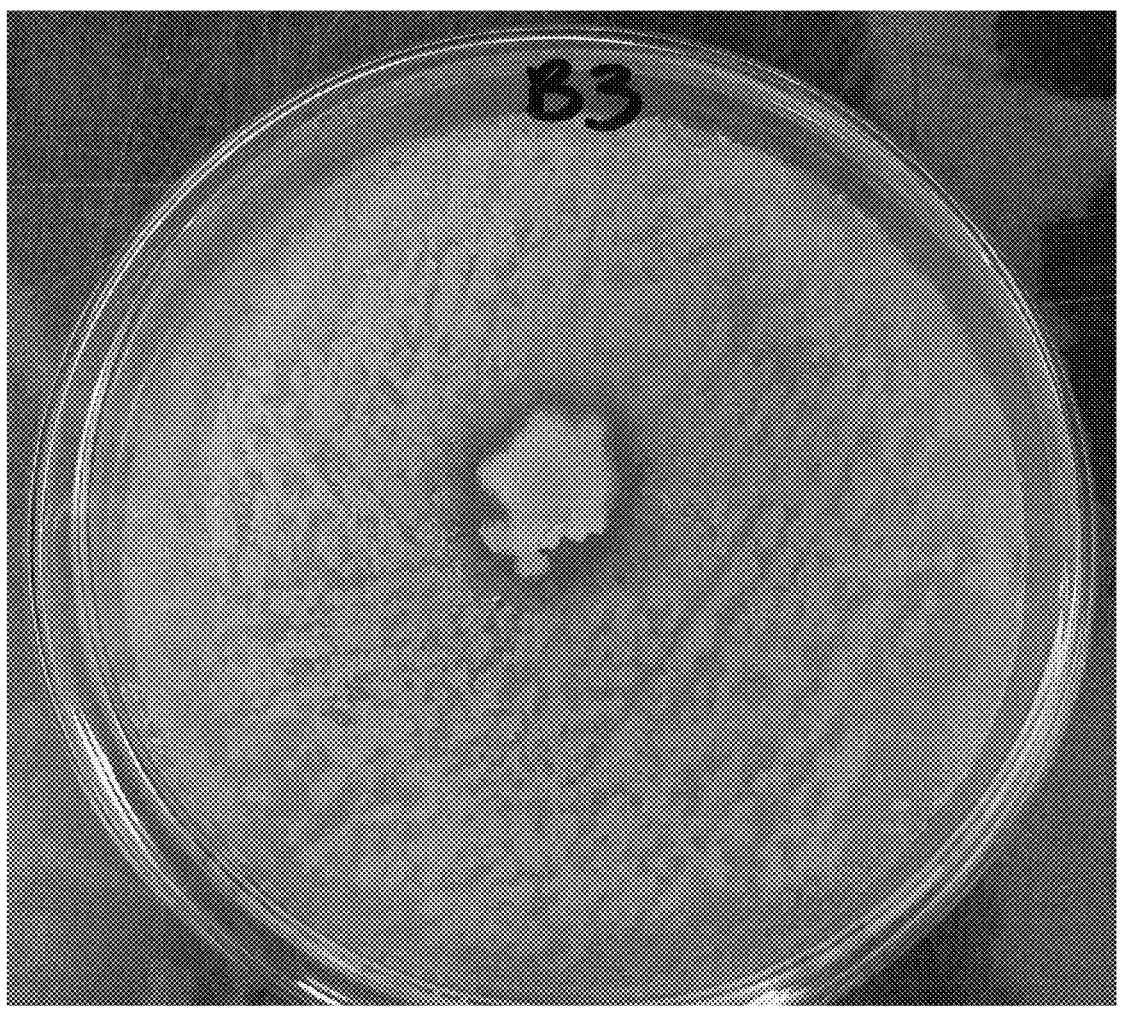
FIG. 6 shows green mold spores spread onto a PDA media plate, and a loop transfer of *Bacillus* spp. added onto plate as well to show the plausible coexistence of the two microorganisms.
Figure 7:
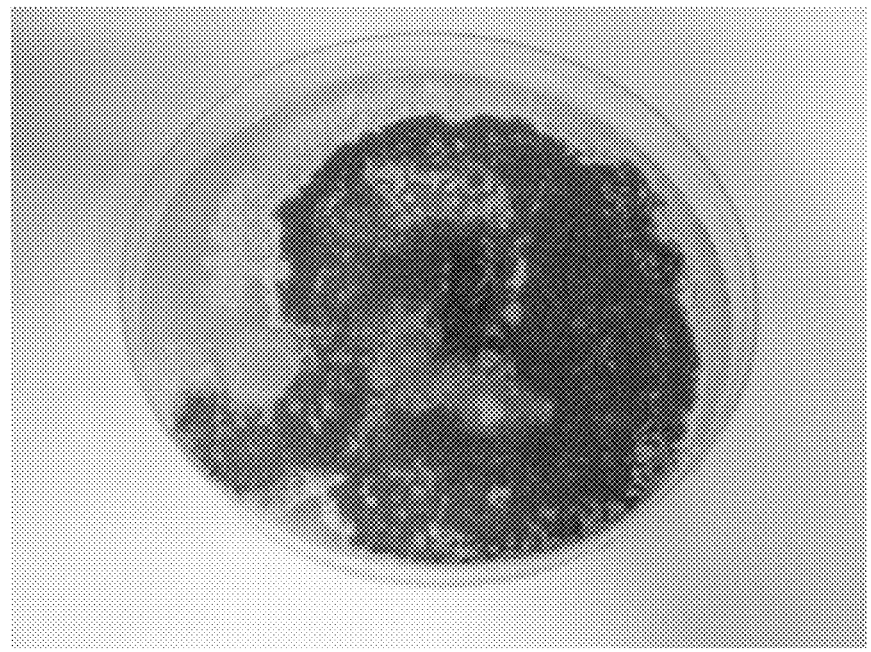
FIG. 7 shows a compost sample divided longitudinally to determine the influence of *Bacillus* spp. culture. Plate A) contained compost only; and Plate B) contained compost with a drop of 1% peptone with overnight culture growth.
Figure 7:
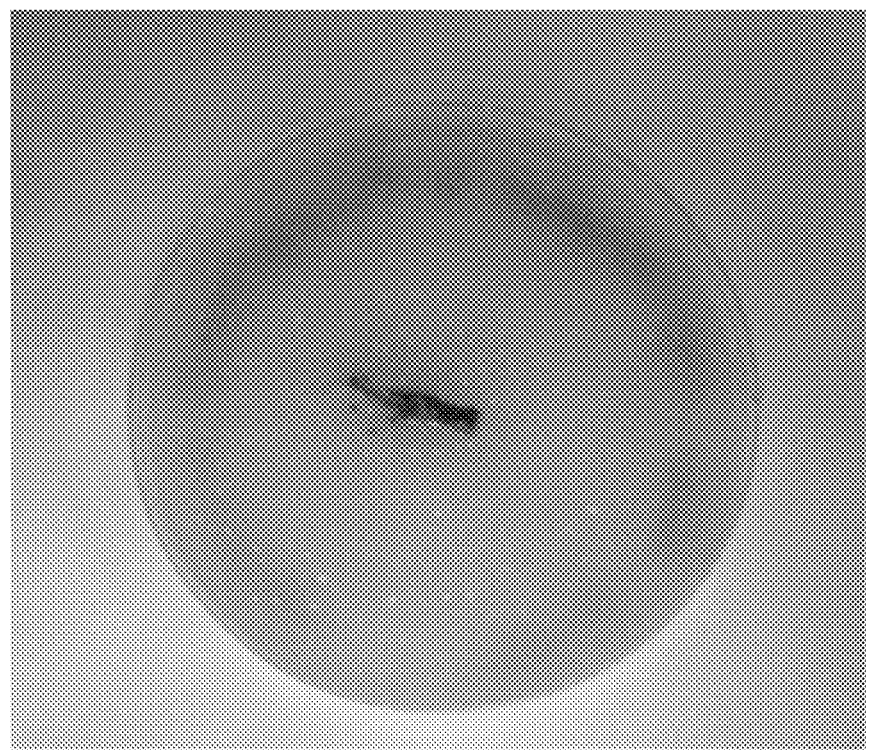

As shown in FIG. 6 and discussed in greater detail in Example 1, the *Bacillus subtilis* culture prevents the growth of green mold when it is added to a plate containing green mold spores. When added to compost that was exhibiting signs of green mold, the culture was able to stop the spread of the green mold in the compost as shown in FIG. 7 demonstrating fungistatic activity. Further studies were conducted to determine whether the culture could stop existing green mold in a cultivation container. The results, illustrated in FIG. 8, suggest that *Bacillus* spp. also has fungicidal activity against *Trichoderma*.

Figure 14:
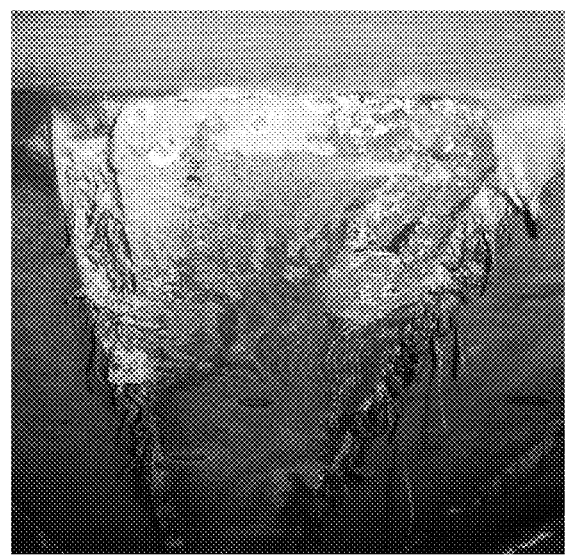
Figure 14:
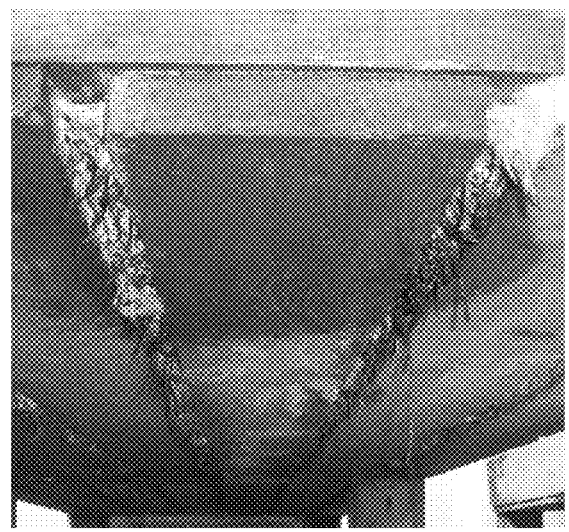
Figure 14:
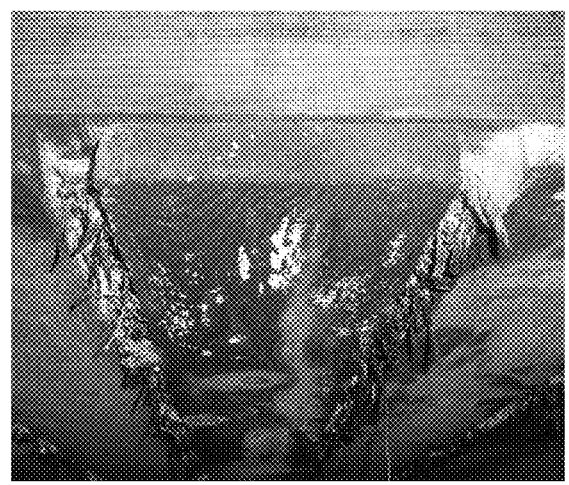
Figure 15:
Figure 15:
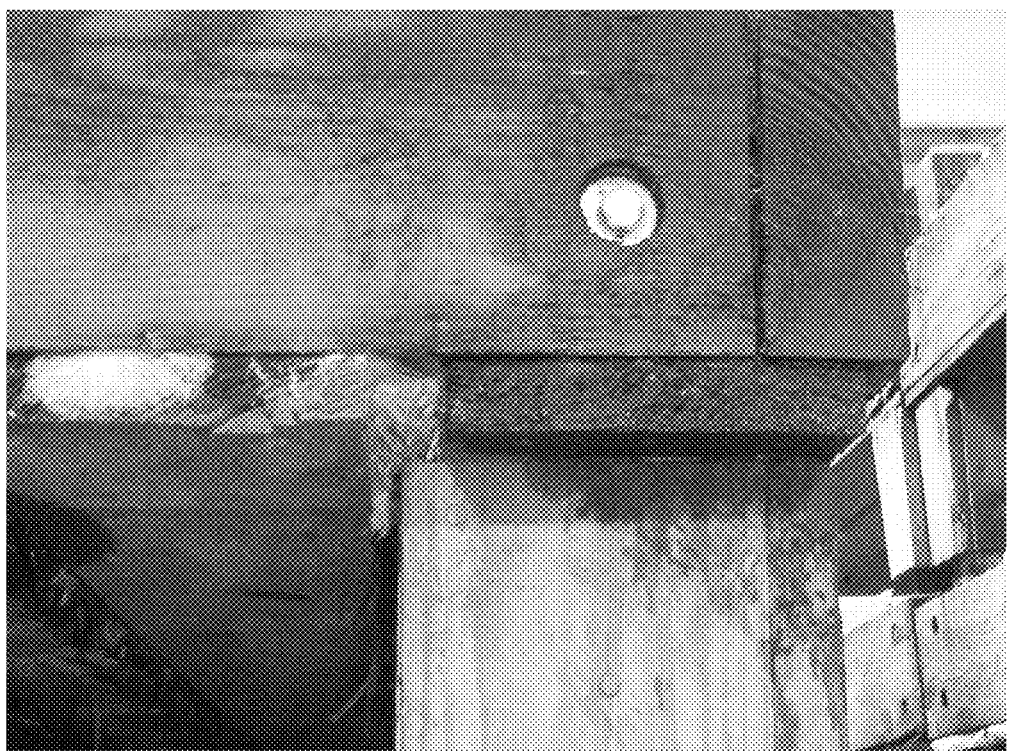

Since spores are spread easily and it can be difficult to completely sterilize all of the equipment used in the production process, controlled testing was done to determine whether the *Bacillus* culture could stop or slow the growth of green mold on pinning room cases. The results shown in FIGS. 9, 10, 11 and 12 and discussed in greater detail in example 4 below, illustrate that the culture was able to prevent the spread of spores. The results also demonstrate that not only was the culture not detrimental to mushroom growth, but that it may actually have beneficial effects on mushroom growth. FIGS. 14 and 15 illustrate that the Bacillus composition was effective on actual pinning room cases.

The *Bacillus* composition is safe to apply to mushroom mycelia. The results shown in FIGS. 16 and 17 demonstrate that mycelia were able to survive being sprayed with the composition. The mycelia may actually grow thicker after being sprayed.

Figure 18:
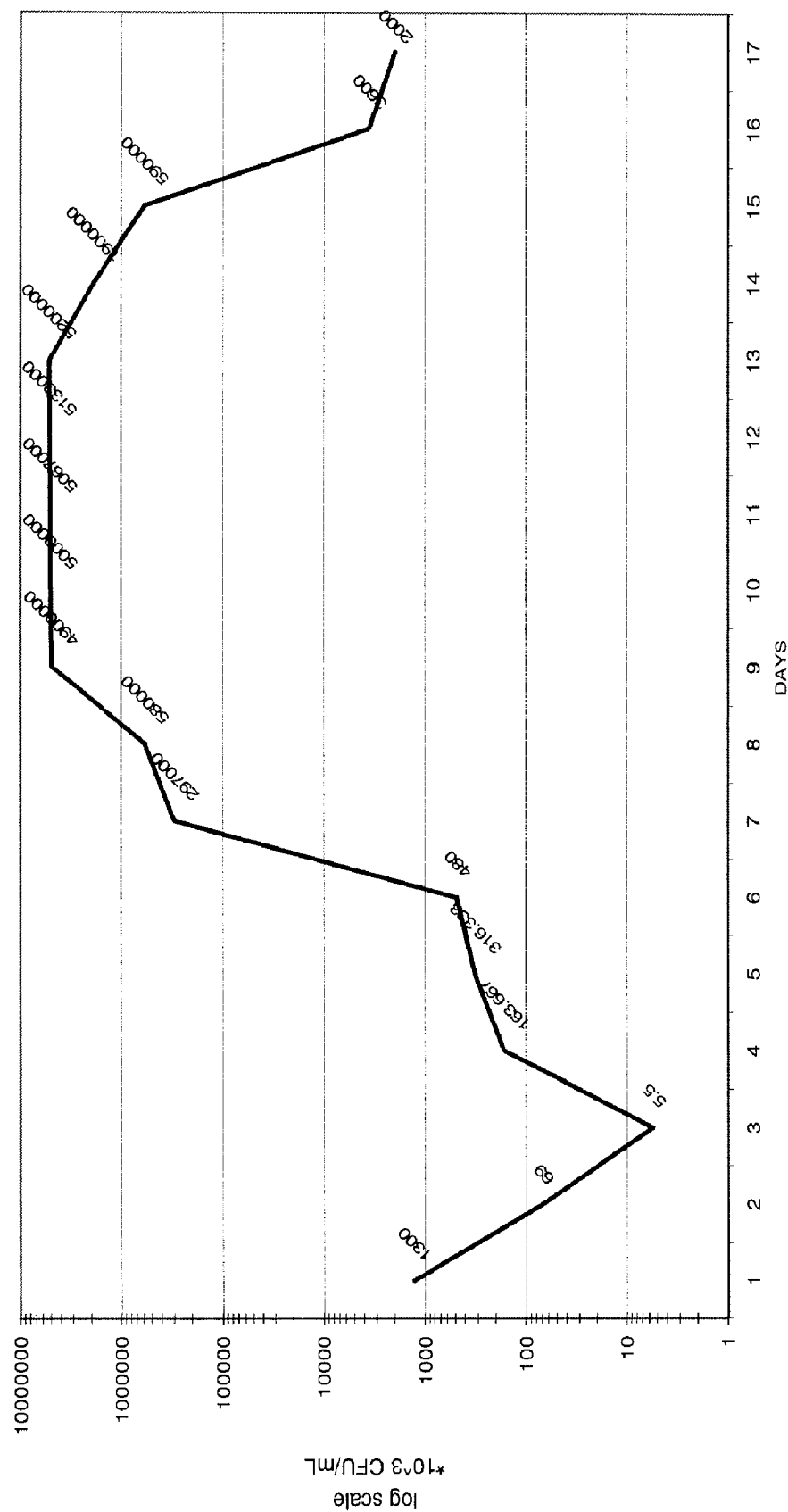

Experiments were performed to determine whether the *Bacillus* could grow in water. FIG. 18 illustrates a growth curve of a *Bacillus* isolate in distilled water. These results indicate that *Bacillus subtilis* can survive and grow in water. This suggests that effective control of mold can be achieved through spraying with water containing the organism. The composition is very cost-effective.

Figure 19:
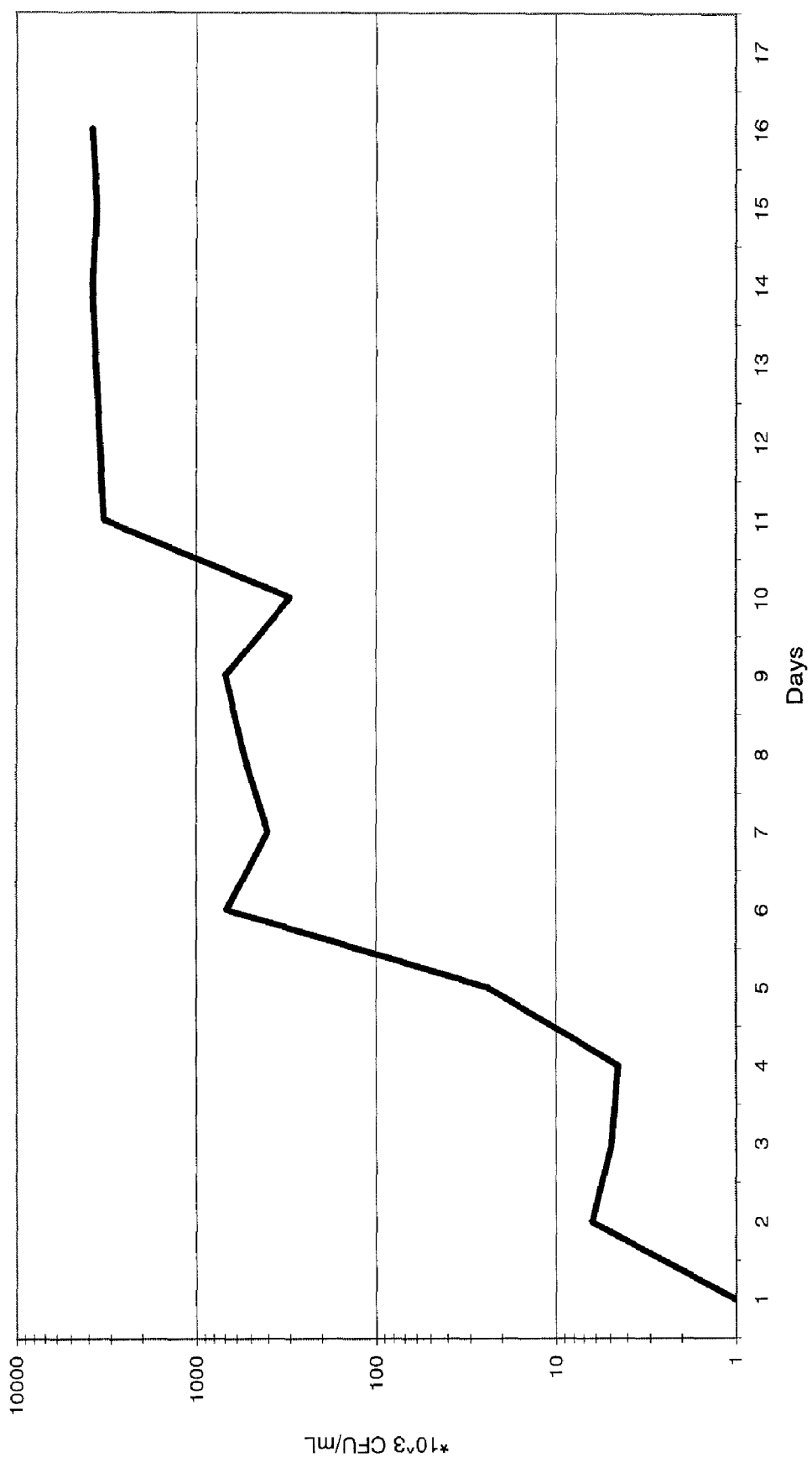

Based on the previous results, samples from inoculated water bottles were added to the spawning water tank. The survival and growth of the culture is shown graphically in FIG. 19. When compost was sprayed with the water, there was a reduction in the prevalence of green mold and healthy mycelium growth was seen.

Figure 20:
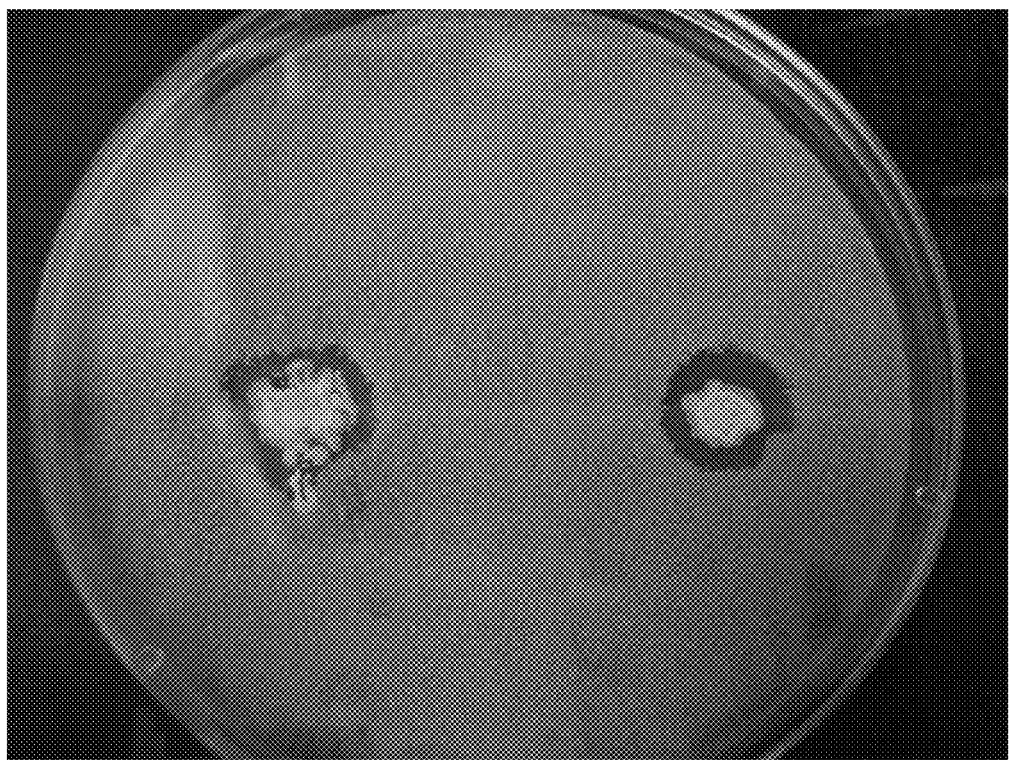

As a further test, daily samples from the tank water were plated together with green mold to determine whether the bacteria were still viable and maintained their antifungal properties. The results shown in FIG. 20 indicate that green mold growth was inhibited in a halo around the bacterial colonies.

The results illustrated in the Figures clearly demonstrate for the first time that *Bacillus subtilis* is an effective biocontrol agent for the prevention or control of green mold in mushroom production.

The above disclosure generally describes the present invention. It is believed that one of ordinary skill in the art can, using the preceding description, make and use the compositions and practice the methods of the present invention. A more complete understanding can be obtained by reference to the following specific examples. These examples are described solely to illustrate preferred embodiments of the present invention and are not intended to limit the scope of the invention. Changes in form and substitution of equivalents are contemplated as circumstances may suggest or render expedient. Other generic configurations will be apparent to one skilled in the art. All reference documents referred to herein are hereby incorporated by reference.

EXAMPLES

Although specific terms have been used in these examples, such terms are intended in a descriptive sense and not for purposes of limitation. Methods of microbiology, molecular biology and chemistry referred to but not explicitly described in the disclosure and these examples are reported in the scientific literature and are well known to those skilled in the art.

Example 1

Prevention of Green Mold

Experiments were done to determine if *Bacillus* spp. could prevent the growth of green mold. Green mold spores from an isolated lawn were spread onto a PDA plate to create a lawn of growth. A single colony transfer from a nutrient agar plate containing *Bacillus* spp. was placed in the center of the plate. Plates were incubated for 72 hours at 22-25° C. A lawn of green mold growth formed around the perimeter of the *Bacillus* culture inoculation site. A halo with zero growth formed between the two microorganisms. The results are shown in FIG. 6. The results indicate that *Bacillus* spp. was able to slow the growth of green mold in the surrounding area when inoculated at the same time.

Example 2

Fungistatic Effects

Experiments were performed to determine if *Bacillus* spp. culture could stop existing green mold growth. A pinning room had green mold growing on pre-case compost. It was uncertain if it was throughout the tray although it was visible from underneath the tray. One straw piece with a section of green mold, white mycelium, as well as natural straw, was collected from in between the slates underneath a tray with gloved hand. This sample was divided into two sections longitudinally; one plated directly onto PDA, and the second with a drop of J-P13 culture grown overnight in 1% peptone and then plated onto PDA. Plates were incubated at 22-25° C. for 72 hours. The results are shown in FIG. 7. The first plate had considerable green mold growth covering 80% of the plate; along with other contaminants from the compost. The second plate had moderate bacterial growth with a few hyphea from the green mold section on the straw. The results indicate that the *Bacillus* spp. culture was able to prevent the spread of green mold.

Example 3

Small Container Cultivation

Figure 8:
FIG. 8 shows the effect of a *Bacillus* spp. culture added to existing mold.
Figure 8:
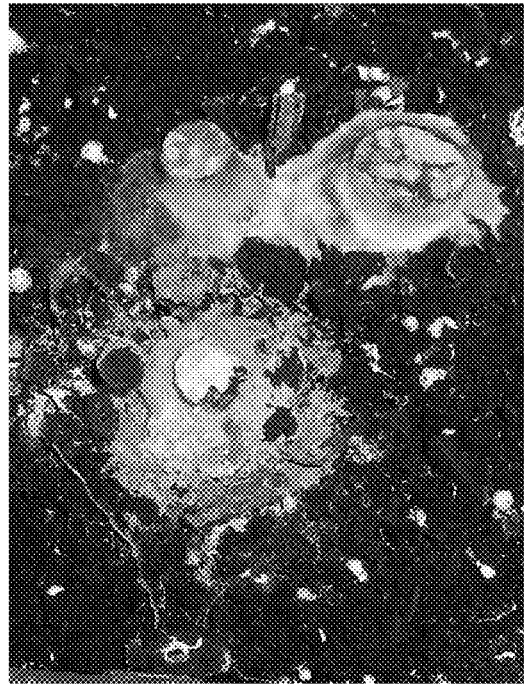
Figure 8:
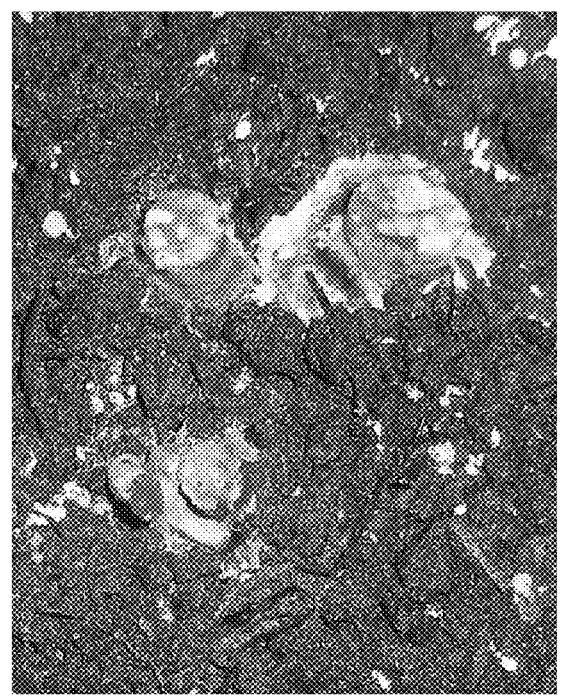

To determine if the *Bacillus* spp. culture could stop or yield existing green mold growth on mushroom stipe in small container cultivation, mushrooms harvested from test trays in the lab were infected with green mold growth on remaining stipe. Approximately 7 mL of a 1% peptone solution containing *Bacillus* spp. culture was poured directly onto the sample. This was repeated 3 and 5 days later. The tray was kept at room temperature throughout. The results are shown in FIG. 8.

The visibly green mold appeared yellow after the first application. After the second application, there was noticeably no green nor yellow mold on the stipe. This suggests that the bacterial culture is fungicidal.

Example 4

Mold in Pinning Room Cases

Experiments were done to determine if *Bacillus* spp. culture can stop or slow the growth of green mold existing atop case in pinning rooms. The mold growing on the actual trays on the farm was assessed.

Figure 9:
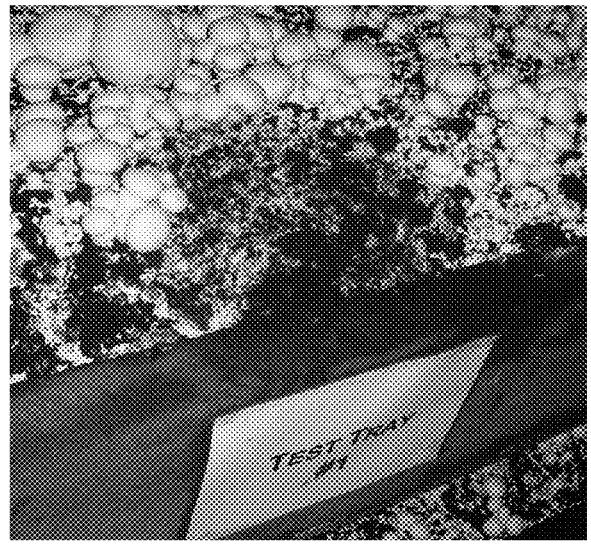
FIG. 9A shows a test tray 1 results after approximately 2 hours of being sprayed with a *Bacillus* culture. 9B shows a test tray 2 after the condensed green mold growth was sprayed. As shown in 9C, test tray 3 had minimal green mold growth and it was barely visible after first being sprayed.
Figure 9:
Figure 9:

Lawns of the *Bacillus* spp. culture were harvested onto four PDA plates and four SMA plates. Plates were incubated at 25° C. for 72 hours and stored at approximately 5° C. until they were collected in 1% peptone about one week later. Using a bent rod, the colonies were gathered and transferred into 800 mL of peptone per flask. In total, two SMA and two PDA plates were added to two separate peptone flasks. Immediately, flask one was diluted with equal amounts of water and peptone culture to create a referenced culture concentration. Using a cleaned 1 L spray bottle, flask one was sprayed onto three test trays with existing green mold, as shown in FIG. 9. Test tray 1 was a small area, with tray 2 the entire tray was sprayed but with a greater amount being sprayed on green mold present on tray, and tray 3 was a small corner area. The test trays were marked so areas would not receive traditional environmental control fungicidal treatments. Test trays were sprayed a few days later with the second flask.

Figure 10:
FIG. 10 shows Isolates of *Bacillus* spp. grown on two PDA plates and one SMA and in three 1 L flasks with approximately 800 mL of 1% peptone.
Figure 11:
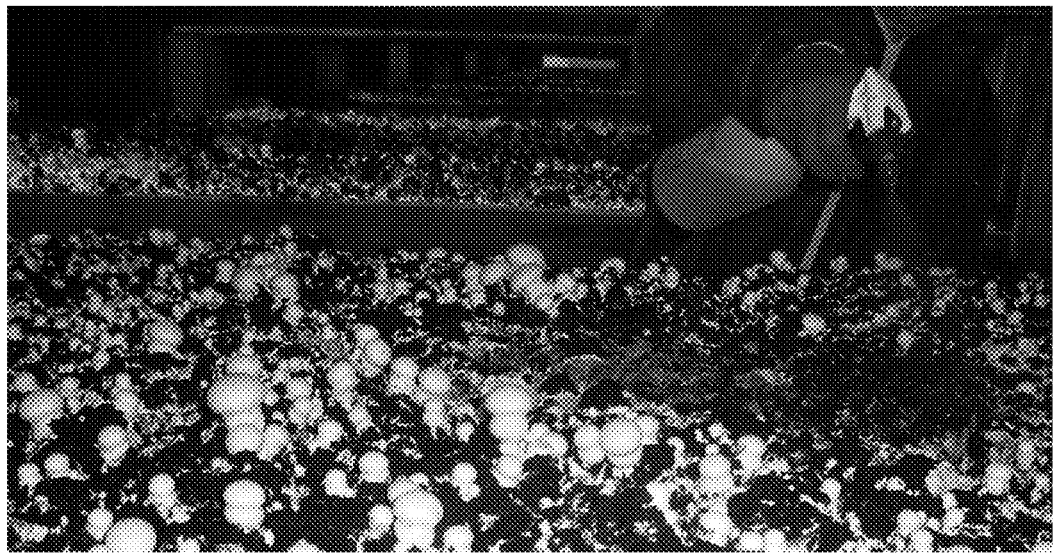
FIG. 11 shows a test tray 2 after second application of *Bacillus* spp. culture covering entire tray, and the resulting observations;
Figure 11:
Figure 12:
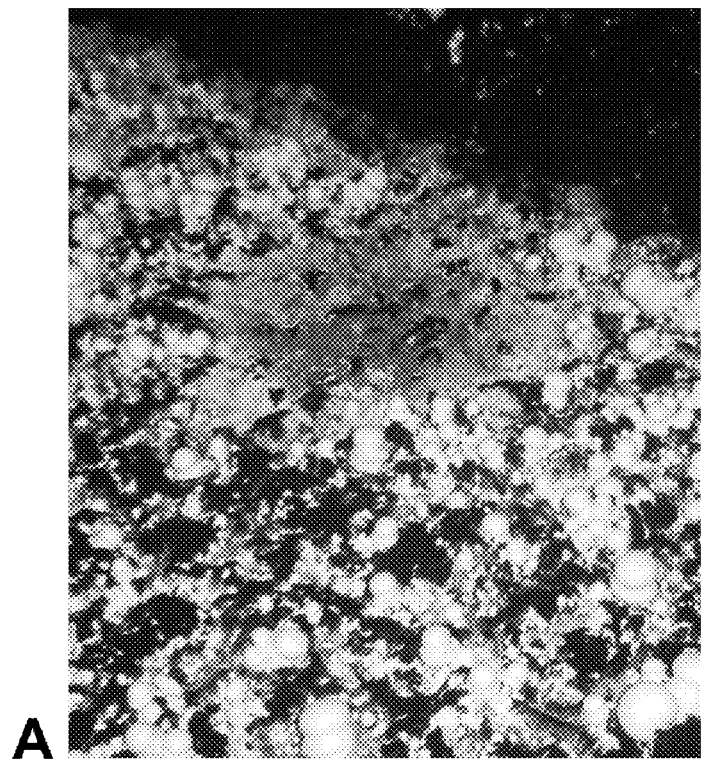
Figure 12:

Flasks #3, 4, and 5 with 800 mL 1% peptone were inoculated with 72 hour harvested bacterial culture with one plate per flask as shown in FIG. 10; and were sprayed onto the same three test trays within 24 hours of the initial inoculation. FIG. 11 shows the effect on test tray 2. The effect on a tray before and after 24 hours of inoculation is shown in FIG. 12.

Flask #6 & 7 were inoculated with one plate per flask. Flask #6 was sprayed within hours of inoculation onto four new test trays. Flask #7 was incubated for 48 hours and diluted with an equal amount of 1% peptone and sprayed onto the same new four test trays.

The results indicate that existing green mold on the test trays could be slowed and even stopped with sufficient *Bacillus* spp. culture. Green mold was minimized on all test trays.

When the culture was sprayed on the perimeter of the contamination within the tray, there was minimal spreading onto the remaining tray. For test tray 2, the entire tray was sprayed with *Bacillus* spp. not only the one concentrated section with green mold. The mold did not spread from the condensed spot, indicating that the *Bacillus* spp. composition prevented the spread of spores. In addition, even though the entire tray was sprayed, very good mushroom production was obtained throughout the tray. This suggests that *Bacillus* spp. was not harmful to mushroom growth. In fact, the mushrooms from test tray 2 were denser than the other trays in the growing room. Also, the second break on test tray 2 came earlier (approximately 1 day) and was larger in size than the remainder of the room as well. This indicates that the mushrooms grow faster as they are better supported by the media.

Figure 13:
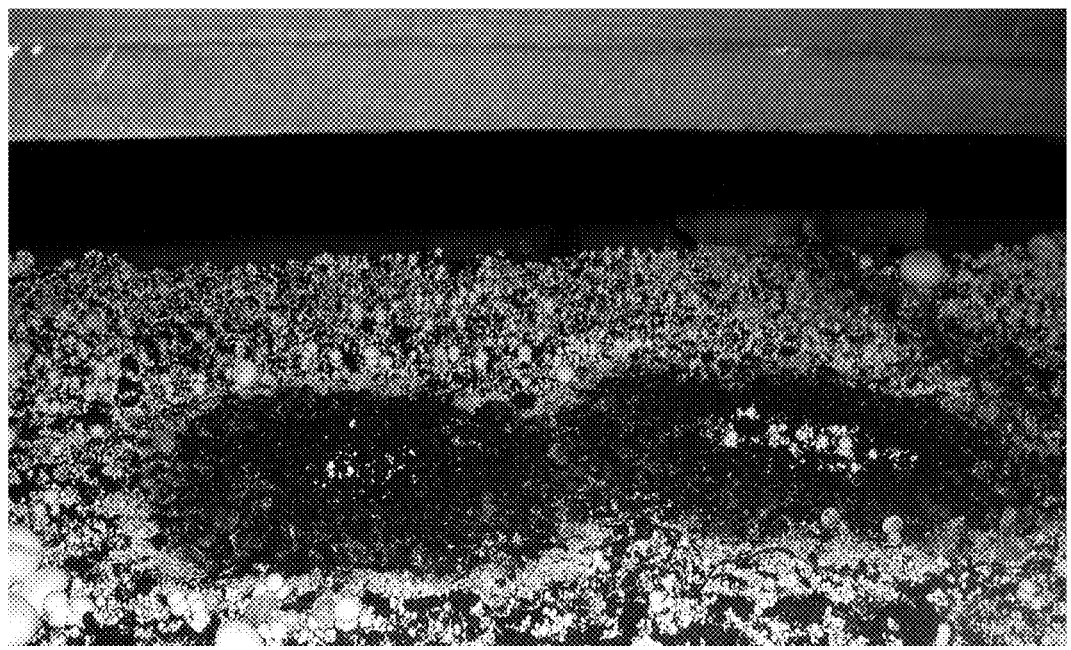
Figure 13:

The existing green mold on the second trial of test trays was also halted by the *Bacillus* spp. culture. With an earlier application, the green mold was inhibited in enough time to allow for pinning to occur, as shown in FIG. 13. This indicates that the antifungal activities of *Bacillus* spp. applies to green mold only and does not have detrimental effects on the commercial mushroom/funti (*Agaricus bisporus*) allowing mycelium growth and mushroom production to continue.

Example 5

Elimination of Green Mold on Trays

To determine if the composition could decrease the amount of green mold growing on trays, and possibly spreading onto product, various green molds found on trays in pinning rooms (the same as the observed test trays) were also tested with the *Bacillus* spp. culture in 1% peptone. Trays were sprayed directly and observed along with test trays. FIG. 14 shows the effect on growth of two types of mold on trays.

Trays are typically recycled. This allows old trays to be contaminated with mold spores that are able to survive steam sterilization. Thus, contamination can occur repeatedly. When the moisture in the room is relatively high, such as in the pinning rooms, *Bacillus* spp. colonies sprayed onto the tray were able to survive, and the mold did not return. Also, when *Bacillus* spp. is sprayed onto visibly contaminated trays in the pinning rooms, there is a decrease in contaminated trays in growing rooms, and thus on the entire farm.

Example 6

Peptone Composition

Figure 16:
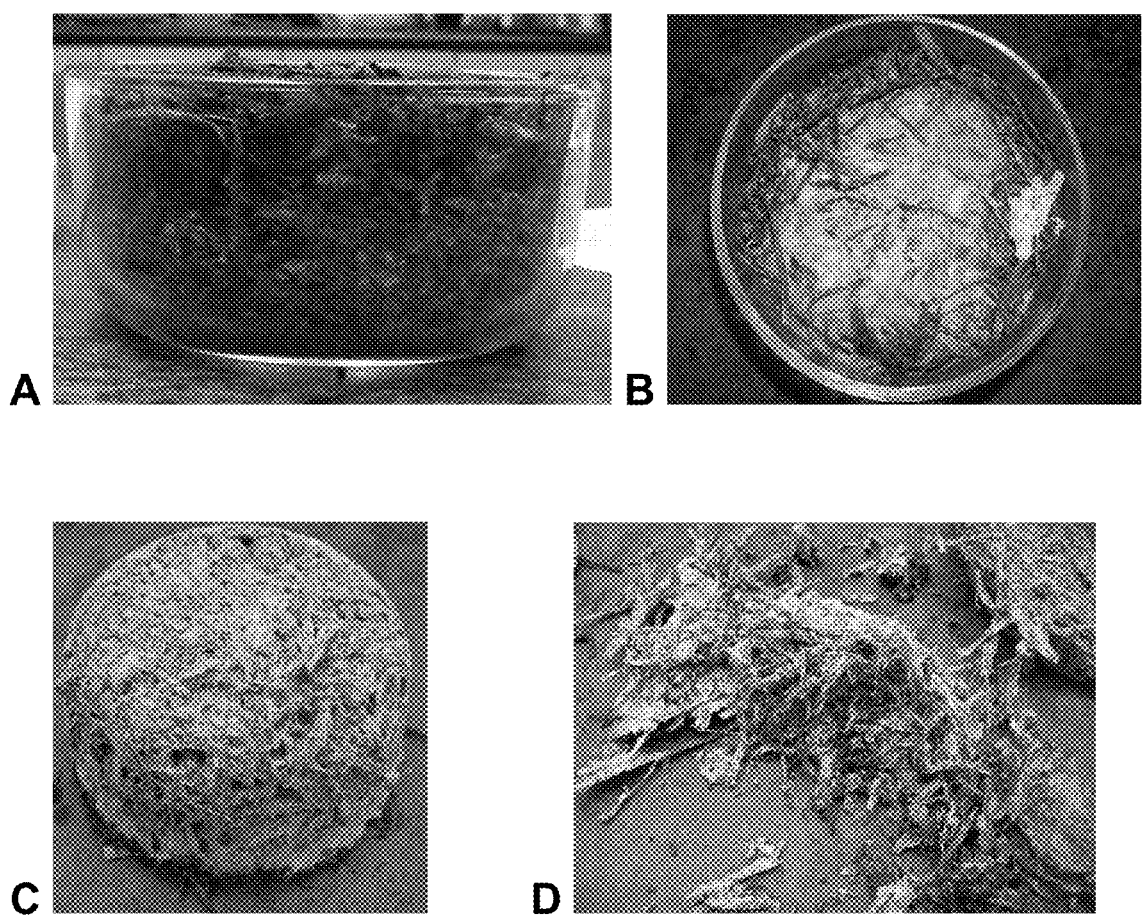
Figure 17:
Figure 17:
Figure 17:
Figure 17:
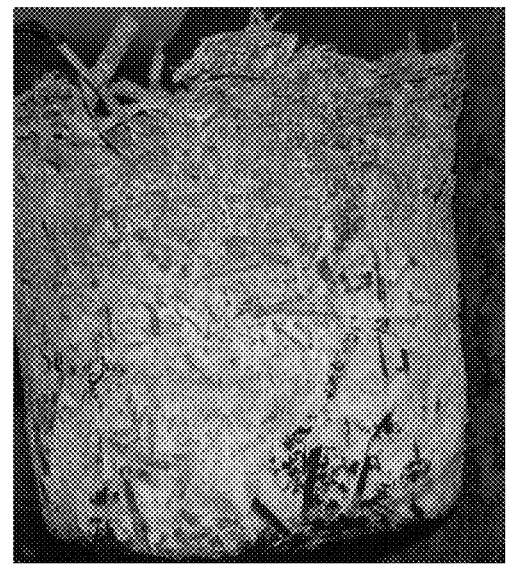

To determine if peptone or *Bacillus* spp. inhibited initial mycelium growth, a precase was spiked with 4 mL of 48 hour, 1% peptone and culture solution. The culture was dispersed using a 5 mL pipette, where the volume was determined based on sample volume weight. The culture was distributed throughout the top 2-3 cm of the sample; wrapped in plastic and incubated at 25.0° C. A second sample (shown in FIG. 17) had an addition of known green mold growth from pinning room 11 (collected and sprayed with culture). The sample container was such that the entire depth of the sample was able to be observed over time. FIG. 16 shows the initial sample preparation, green mold found, and the final growth of mycelium. The mixture of mycelium and *Bacillus* spp. showed that mycelium were indeed able to survive. Furthermore, there was no growth of green mold on the areas that were sprayed. The mycelia developed, and it may even be suggested that thicker mycelium developed with the culture. The second sample showed that the green mold did not dominate the precase, and that the addition of *Bacillus* spp. did not inhibit mycelium growth.

Example 7

Aqueous Solution

To determine if *Bacillus* spp. was able to survive in water, an aqueous solution was prepared. Initial tests were a present/absence test in the determination of *Bacillus* spp. survival in water. Water samples were collected from the spawning water tank at the tunnels, the office kitchen, as well as a sterilized distilled water sample as a control. 90 mL water samples were innoculated with 1 mL of 24 hour 1% peptone solution. As well, 10 mL water samples were inoculated with a loopful of culture. Spread plates were done on SMA, and gram stains were performed on the isolates. The results indicated that the

*Bacillus* spp. was indeed able to grow in aqueous solution with zero additional nutrients.

Example 8

Growth Curve

Since it was determined that *Bacillus* spp. were able to survive in water without any supplementation, the growth curve was determined.

One plate of culture with 48 hours growth was used per 20 L distilled water bottle, which contained approximately 18.9-19 L of water. Preferred technique used for culture collection was to pour 9 mL sterilized distilled water, collected with spreader, and transferred into an empty sterile tube via 1.0 mL micropipette. This tube was then poured directly into the bottle, and the tube was washed with sterilized distilled water to ensure ample culture was transferred.

The water bottles were agitated periodically to ensure proper distribution of culture, and were kept at 22-25° C. Samples were collected approximately every 24 hours for dilution and plating to determine the population. The first bottle, identified as batch 22, was plated to distinction to determine that target growth bracket per day per bottle. Target dilutions were made with subsequent bottles in accordance to the previous days growth & the initial bottle counts. Spread plates required 36-48 hours at 25.0° C. for optimal colony recovery; with countable plates between 30-300 CFU/mL. If counts were not in the range, counts were considered estimates. In order to compare the rate of growth, a 900 mL sample of batch 22 was stored in the incubator at a known 25° C., as well as batch 21 with 1% peptone. Comparison counts were made periodically to observe populations growths with different nutrient availability, and the effects of temperature.

Counts were recorded, with at least 4 samples for each day recorded. Each bottle was graphed independently, and an average growth curve was created as shown in FIG. 18.

The doubling rate of *Bacillus* spp. was determined to be approximately 7 hours using viable culture counts measured at 24 hour intervals. The counts were used to form a linear (not shown) and logarithmic growth curve (FIG. 18), showing a graph of the number of cells counted at different time points. Given that the cells were transferred from a solid to liquid media, the concentration had a timely lag period, requiring at least 4 days to recover from the transfer. Therefore substantial culture death did occur prior to the population recovery. An exponential rate of growth was observed after 3 to 4 days, indicating that the culture was able to adjust to the new medium (distilled water). The bacteria continues to divide regularly by the process of binary fission. By plotting the linear graph onto a logarithmic scale (FIG. 18), an almost straight line indicated that the growth was indeed exponential.

Limited growth was observed after 14 days, where the stationary phase population declined exponentially resulting in the death phase. The generation time was calculated during the exponential phase of growth (day 5 to day 9); $X=2^n \cdot X_o$ where $X_o$ is the initial number of cells, n is the number of generations, and X is the number of cells after n generations. This generation time was specific to the media used, and the environmental conditions of the incubation period. At a higher temperature, the growth rate increases as demonstrated with the smaller aliquot from batch 22 that had a log 2 increase. The 1% peptone sample had a log 3 increase; but resulted with the death phase occurring 7 days earlier.

Example 9

Addition of *Bacillus* to Spawn Water Tank

Experiments were performed to determine the effects of *Bacillus* spp. being added to the spawn water tank at the tunnels to incorporate the antifungal properties into the compost. The initial water bottles could be used after seven days incubation for the desired concentration. This is also the beginning of the stationary phase as shown in FIG. 18, allowing for optimal populations to occur.

Bottles should preferably be maintained between 15-32° C., where the optimal temperature would be 22-25° C. If the temperature is not within this range, sporulation may occur, resulting in dormant culture and lack of activity. The water bottles were added to the spawn water tank a minimum of 10-12 hours, to a maximum of 72 hours prior to spawning. Samples from the spawn water tank were taken in the morning prior to spawning, and counts were made as per section I as shown in FIG. 19.

In addition, the tank water samples from each morning were plated with green mold to determine that the culture was still valuable; ensuring antifungal properties were still present (FIG. 20). The method of spray of the spawn water tank onto the freshly pasteurized compost was jet line, and thus not well-distributed. The water from the tank was not consistent throughout the compost; allowing for a higher concentration of culture in some sections, and extremely low concentration in others. Ideally, the water density distribution would be such that there is an overlap between each spray nozzle by at least 30%, along with adequate absorption and mixing throughout the compost to create a homogenous mixture.

FIG. 19 illustrates that the *Bacillus* spp. added to the spawn water tank were indeed able to survive, and grow exponentially. The counts were not cumulative due to the almost daily emptying of the spawn tank. It was found that with the addition of two 7 day-bottles; the water counts were of the optimal concentrations, allowing for the possibility of the desired 50% green mold inhibition levels as shown in FIG. 20. When the compost sprayed with the water containing the initial bottle water is sent to case, there is reduction in green mold and good mycelium growth is seen.

What is claimed is:

1. A biologically pure culture of *Bacillus subtilis* strain J-P13.

2. A composition comprising a biologically pure culture of *Bacillus subtilis* strain J-P13 in an effective amount and a carrier, for the control of green mold infection of mushrooms by *Trichoderma harzianum*.

3. The composition of claim 1, wherein the carrier is selected from the group consisting of microcarrier beads, granules, particles, peptone solution, oil, wax, gel, and water.

4. The composition of claim 3, wherein the carrier is water.

5. A process for controlling *Trichoderma harzianum* in a mushroom, the process comprising applying the composition of claim 1 to the mushroom.

6. The process according to claim 5, wherein the composition is applied by spraying.

7. The process according to claim 5, wherein the composition is an aqueous composition.

* * * * *